United States Patent [19]

Nader

[11] Patent Number: 4,950,802

[45] Date of Patent: Aug. 21, 1990

[54] PROCESS FOR THE PREPARATION OF ARYL TRIFLUOROMETHYL ETHERS

[75] Inventor: Bassam S. Nader, Midland, Mich.

[73] Assignee: The Dow Chemical Company, Midland, Mich.

[21] Appl. No.: 282,805

[22] Filed: Dec. 9, 1988

[51] Int. Cl.$^5$ .............................................. C07C 85/14
[52] U.S. Cl. .................................. 568/655; 558/423; 558/424; 564/441; 564/442
[58] Field of Search ................ 568/655, 588; 558/423, 558/424; 564/441, 442

[56] References Cited

U.S. PATENT DOCUMENTS

| | | | |
|---|---|---|---|
| 4,093,665 | 6/1978 | Belous et al. | 260/612 D |
| 4,157,344 | 6/1979 | Feiring | 260/575 |
| 4,207,266 | 6/1980 | Opie | 568/655 |
| 4,600,787 | 7/1986 | Marhold et al. | 549/362 |
| 4,620,040 | 10/1986 | Alsop | 568/656 |

OTHER PUBLICATIONS

R. Chambers, "Preparation of Highly Fluorinated Compounds", *Fluorine In Organic Chemistry*, pp. 14–21, (1973).

A. Feiring, "Chemistry in Hydrogen Fluoride. 7. A Novel Synthesis of Aryl Trifluoromethyl Ethers", 44 *J. Org. Chem.*, pp. 2907–2910, (1979).

A. Barbour et al., "The Preparation of Organic Fluorine Compounds by Halogen Exchange", *Advances in Fluorine Chemistry*, pp. 181–270, (1963).

*Primary Examiner*—Bruce Gray

[57] ABSTRACT

A novel method for the preparation of aryl trifluoromethyl ethers which comprises reacting a phenol, a perhalomethane, and an antimony pentahalide. For example, 4-nitrophenol may be reacted with an excess over stoichiometry of both carbon tetrachloride and antimony trifluoride with a catalytic amount of antimony pentachloride to form 4-nitrophenyl trifluoromethyl ether.

15 Claims, No Drawings

PROCESS FOR THE PREPARATION OF ARYL TRIFLUOROMETHYL ETHERS

BACKGROUND OF THE INVENTION

The present invention relates to a process for the preparation of aryl trifluoromethyl ethers. More specifically, the present invention relates to such a process which comprises contacting a phenol with at least one perhalomethane and at least one fluorinating agent.

Aryl trifluoromethyl ethers are useful as intermediates for a variety of applications, including agricultural and pharmaceutical applications, functional and tribological systems, and polymers. Various reactions are known wherein aryl fluoromethyl ethers can be prepared from aryl halomethyl ethers with non-fluoro halo substituents. For example, U.S. Pat. 4,620,040 discloses a process for the preparation of aryl trifluoromethyl ethers in which a trichloroanisole is reacted with hydrogen fluoride in the presence of a fluorinated alumina catalyst. U.S. Pat. No. 4,600,787 discloses a two-step process for partially fluorinating perhalogenated anisoles with hydrogen fluoride or alkali metal fluorides, and then treating the partially-fluorinated anisoles with catalysts such as halides of boron, aluminum, tin, arsenic, antimony, titanium, molybdenum and iron.

U.S. Pat. No. 4,093,665 discloses a process for the fluorination of aryl perfluoroalkyl ethers using sulfur tetrafluoride in hydrogen fluoride solution. French Pat. No. 2,214,674 discloses a process for the fluorination of aryl chlorothioformates with molybdenum hexafluoride. U.S. Pat. No. 4,157,344 discloses a one-step process for the production of aryl trifluoromethyl ethers in which a phenolic compound is reacted with a perhalomethane in the presence of at least three molar equivalents of hydrogen fluoride.

The processes described above require a two-step process involving the production of aryl perhalogenated intermediate materials and/or require the use of harsh fluorinating agents such as hydrogen fluoride. It would be advantageous to provide a one-step process for the production of aryl trifluoromethyl ethers which does not require the use of hydrogen fluoride as a fluorinating agent.

SUMMARY OF THE INVENTION

The present invention is a method for the preparation of aryl trifluoromethyl ethers which comprises contacting:

(a) a phenolic compound wherein the ortho substituents are sterically compatible with the OH group and do not substantially reduce the reactivity thereof; with (b) a compound of the following formula:

CCl$_3$ wherein X is a halogen, C$_{1-10}$ alkyl, C$_{1-10}$ perhaloalkyl, alkyl polyether, or a perfluoroalkyl polyether moiety of the following formula

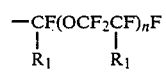

$$-\underset{R_1}{CF}(O\underset{R_1}{CF_2CF})_nF$$

wherein R$_1$ is H or F or CF$_3$, and n is a whole number from 1-10; in the presence of (c) a fluoroantimony polyhalide: under conditions sufficient to form an aryl trifluoromethyl ether. The amount of reactants (b) and (c) are each in excess of the stoichiometric amount needed, respectively, for displacement of the hydrogen of the phenolic OH function of reactant (a), and for substantial conversion of the chloro groups derived from component (b) to fluoro groups.

The present invention is a one-step process for the preparation of aryl trifluoromethyl ethers. This process utilizes phenols as starting materials, instead of requiring the preparation of aryl perhalogenated starting materials suitable for fluorination. In addition, this process utilizes antimony halides, which obviates the need for use of harsher or more corrosive fluorinating agents such as hydrogen fluoride, sulfur tetrafluoride, or equally harsh fluorinating agents. Third, this process employs fluorinating agents which are non-gaseous at ambient temperatures and pressures, which gives material handling advantages. These advantages and others of this invention will be apparent in the description which follows.

DETAILED DESCRIPTION OF THE INVENTION

The phenolic compound employed in this process is a phenol with hydrogen in the ortho, meta, and para positions relative to the hydroxyl groups. This compound optionally has substituted thereon one or more substituents in the ortho, meta, and para positions relative to the hydroxyl groups. The ortho substituents of this compound are those which are sterically compatible with the OH group and do not substantially reduce the reactivity thereof and include halo, perhaloalkyl, alkyl, or cyano moieties. In the preferred embodiment, the phenolic compound is of the formula

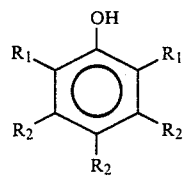

wherein R$_1$ independently in each occurrence is hydrogen, or a halogen, perhaloalkyl, alkyl, or cyano moiety, which is sterically compatible with the OH group and does not substantially reduce the reactivity thereof, and R$_2$ is independently in each occurrence hydrogen or a halogen, perhaloalkyl, alkyl, cyano, hydroxy, amino, or nitro moiety. The meta and para substituents of this compound include halo, perhaloalkyl, alkyl, cyano, hydroxy, amino, nitro, or hydrogen moieties. The preferred phenolic compounds of this process include 4-nitrophenol and 3-nitrophenol. Preferably, these substituents are stable, i.e., resistant to the action of antimony halides under reaction conditions.

The compound of component (b) of this invention is of the following formula:

CCl$_3$X wherein X is a halo, C$_{1-10}$ alkyl, C$_{1-10}$ perhaloalkyl, alkyl polyether, or perhaloalkyl polyether moiety of the following formula

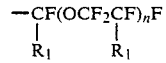

$$-\underset{R_1}{CF}(O\underset{R_1}{CF_2CF})_nF$$

wherein R₁ is H or F or CF₃, from 1-10. The preferred compounds of this component include carbon tetrachloride and fluorotrichloromethane.

The fluoroantimony polyhalide of this invention is a trivalent fluorohaloantimony, or a pentavalent antimony of the following formula:

SbFY₄ wherein each Y is independently halo, i.e. a fluoro, chloro, bromo, or iodo.

This anhydrous fluoroantimony polyhalide may be obtained commercially or prepared by any known method. For example, commercially available antimony trifluoride or antimony pentafluoride may be employed. Antimony halides which are supported on a substrate may also be employed. For example, Graphimet ™, a solid product sold by Alfa Chemical Co., which consists of a mixture of antimony pentafluoride and graphite containing about 50 percent by weight antimony pentafluoride, may give handling advantages over pure antimony pentafluoride, which is a liquid at ambient temperatures and pressures.

The preferred fluoroantimony polyhalides for use in the method of this invention are the pentavalent antimonys described above, since they are more vigorous fluorinating agents. In addition to the commercially available antimony pentahalides described above, or the same prepared before contact with the other elements of the invention, the fluoroantimony pentahalide may be prepared in situ by, for example, a reaction between antimony trifluoride and a catalytic amount of a pentavalent antimony such as, for example, antimony pentachloride. These fluoroantimony pentahalides are the most preferred for use in the process of the invention for their ease of preparation. The term "catalytic amount" as used herein means an amount ranging from about 1 to about 10 molar percent of the amount of antimony trifluoride. Other methods of conversion of antimony trifluoride to a pentavalent state are generally described in Barbour et al., "The Preparation of Organic Fluorine Compounds by Halogen Exchange" in *Advances in Fluorine Chemistry*, Vol. 3, p. 181-271 (1963).

If the pentavalent antimony is prepared in situ from antimony trifluoride, the process of this invention has handling advantages over processes which employ only gaseous halides such as hydrogen fluoride, or sulfur tetrafluoride, since antimony trifluoride is a solid at ambient temperatures and pressures. In addition, the use of solid or liquid antimony halides lowers the reaction pressures necessary to contain and carry out the process of this invention.

The process of this invention may be carried out in any suitable reaction vessel. Preferred reaction temperatures depend on the reactivity of the particular phenolic compound employed and may range from about 75° C to about 200° C. More preferably, the optimum reaction temperature is above about 110° C, most preferably above about 140° C. More preferably, the optimum reaction temperature is below 180° and most preferably below about 150° C. Reaction times vary according to the reactivity of the particular phenolic compound and the reaction temperature.

Molar ratios of the fluorantimony pentahalide, component (b), and phenolic compound used in the process of the invention are approximately equivalent. However, it is preferable to employ an excess over stoichiometry of the fluoroantimony polyhalide and component (b), relative to the amount of phenolic compound, in order to facilitate their reaction with the phenolic compound. Preferred molar ratios of fluoroantimony polyhalide:phenolic compound range from about 1:1 to about 10:1, more preferably from about 1:1 to about 7 1, most preferably from about 1:1 to about 5:1. Preferred molar ratios of component (b):phenolic compound range from about 1:1 to about 10:1, more preferably from about 1:1 to about 7:1, most preferably from about 1:1 to about 5:1. The process of the invention may be carried out neat or in solution.

The aryl trifluoromethyl ether may be separated from the reaction mixture by any standard separation technique, including, for example, distillation and recrystallization. In one preferred embodiment, the aryl trifluoromethyl ether is readily separated from the reaction mixture by first neutralizing the reaction mixture and then separating the aryl trifluoromethyl ether by steam distillation. The yield of the aryl trifluoromethyl ether product is preferably greater than about 25 percent, more preferably greater than about 40 percent, and most preferably greater than about 60 percent.

ILLUSTRATIVE EMBODIMENTS

The following examples are given to illustrate the invention and should not be interpreted as limiting it in any way. Unless stated otherwise, all parts and percentages are given by weight.

EXAMPLE 1

Conversion of 4-nitrophenol to 4 nitrophenyl trifluoromethyl ether

A 300 cc Parr reactor (steel) equipped with a sealed mechanical stirrer and an internal thermocouple is dried, flushed with nitrogen and charged with 4-nitrophenol (1.4 g, 10 mmol), anhydrous carbon tetrachloride (4 ml, 41.4 mmol), anhydrous antimony trifluoride (5.5 g, 30.8 mmol), and a catalytic amount of antimony pentachloride (0.1 ml, 0.77 mmol). The reactor is then sealed and heated at 150° C (internal) with vigorous stirring for 6.5 hours. Subsequently, the reaction vessel is opened and the contents partitioned between ether and saturated NaHCO₃.Concentration of the organic extract, and flash chromatography of the concentrate produces a 29 percent yield of the desired product.

EXAMPLE 2

Conversion of 3-nitrophenol to 3 nitrophenyl trifluoromethyl ether

Using the same reactor setup as in Example 1, the reactor is charged with 3-nitrophenol (13.9 g, 0.1 mol), anhydrous carbon tetrachloride (38 ml, 0.39 mol), anhydrous antimony trifluoride (53.6 g, 0.3 mol) and a catalytic amount of antimony pentachloride (1 ml, 7.7 mmol). The reactor is then sealed and heated at 150° C (internal) with vigorous stirring for 5.5 hours. Subsequently, the reactor is opened and the contents neutralized with saturated NaHC03 The product is separated by steam distillation, and a 62 percent yield of the product is obtained.

What is claimed is:

1. The process of preparing an aryl trifluoromethyl ether which consists essentially of contacting:
   (a) a phenolic compound wherein the ortho substituents are sterically compatible with the OH group and do not substantially reduce the reactivity thereof; with (b) a compound of the following formula:

CCl₃X wherein X is a halogen, $C_{1-10}$ alkyl, $C_{1-10}$ perhaloalkyl, alkyl polyether, or a perfluoro-alkyl polyether moiety of the following formula

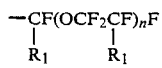

wherein $R_1$ is H or F or $C_3$, and n is a whole number form 1–10; in the presence of
(c) a fluoroantimony pentahalide;
under conditions sufficient to form an aryl trifluoromethyl ether, wherein the molar ratios of fluoroantimony pentahalide:phenolic compound and component (b):phenolic compound are each in the range of from about 1:1 to about 10:1.

2. The process of claim 1 wherein the phenolic compound of component (a) is represented by the following formula:

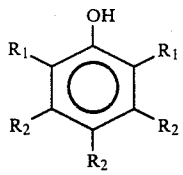

wherein $R_1$ independently in each occurrence is hydrogen, or a halogen, perhaloalkyl, alkyl, or cyano moiety, which is sterically compatible with the OH group and does not substantially reduce the reactivity thereof, and $R_2$ is independently in each occurrence hydrogen or a halogen, perhaloalkyl, alkyl, cyano, hydroxy, amino, or nitro moiety.

3. The process of claim 1 wherein the compound of component (b) is carbon tetrachloride.

4. The process of claim 1 wherein the fluoroantimony polyhalide is the in situ reaction product of antimony trichloride and a catalytic amount of antimony pentachloride.

5. The process of claim 1 wherein the compound of component (a) is 3-nitrophenol.

6. The process of claim 1 wherein the compound of component (a) is 4-nitrophenol.

7. The process of claim 1 wherein the reaction temperature is above about 110° C.

8. The process of claim 7 wherein the reaction temperature is above about 140° C.

9. The process of claim 1 wherein the yield of aryl trifluoromethyl ether product is above about 25 percent.

10. The process of claim 1 wherein the yield of aryl trifluoromethyl ether product is above about 40 percent.

11. The process of claim 1 wherein the yield of aryl trifluoromethyl ether product is above about 60 percent.

12. The process of claim 1 wherein the molar ratio of fluoroantimony polyhalide:phenolic compound ranges from about 1:1 to about 7:1.

13. The process of claim 1 wherein the molar ratio of fluoroantimony polyhalide:phenolic compound ranges from about 1:1 to about 5:1.

14. The process of claim 1 wherein the molar ratio of component (b):phenolic compound ranges from about 1:1 to about 7:1.

15. The process of claim 1 wherein the molar ratio of component (b):phenolic compound ranges from about 1:1 to about 5:1.

* * * * *